United States Patent [19]

Shutt

[11] 3,989,359

[45] Nov. 2, 1976

[54] SELF-EXAMINING GENITAL MIRROR

[76] Inventor: Dolores C. Shutt, 7447 S. Shore Drive, Chicago, Ill. 60649

[22] Filed: Nov. 6, 1973

[21] Appl. No.: 413,251

[52] U.S. Cl. .................................. 350/288; 128/21
[51] Int. Cl.² ...................... G02B 5/08; G02B 5/12
[58] Field of Search ............ 128/6, 21, 22; 240/4.2; 350/288, 296

[56] References Cited
UNITED STATES PATENTS

| 1,989,437 | 1/1935 | Weisz | 350/296 |
| 2,222,167 | 11/1940 | Brandenburg | 128/21 |
| 2,559,290 | 7/1951 | Engelmann | 350/288 |
| 3,075,516 | 1/1963 | Strauch | 128/6 |

FOREIGN PATENTS OR APPLICATIONS

| 237,332 | 6/1969 | U.S.S.R. | 128/21 |

Primary Examiner—Alfred E. Smith
Assistant Examiner—B. C. Anderson
Attorney, Agent, or Firm—Diller, Brown, Ramik & Wight

[57] ABSTRACT

This disclosure relates to a device particularly adapted for hygienic purposes and includes mirror means for visually inspecting vaginal and/or genital areas of a person, particularly when in a seated position, and means for attaching the mirror means to a toilet and/or commode seat. The attaching means including a generally S-shaped element to which the mirror means is attached by a conventional universal joint for adjusting the position of the mirror means to accommodate optical adjustments.

4 Claims, 6 Drawing Figures

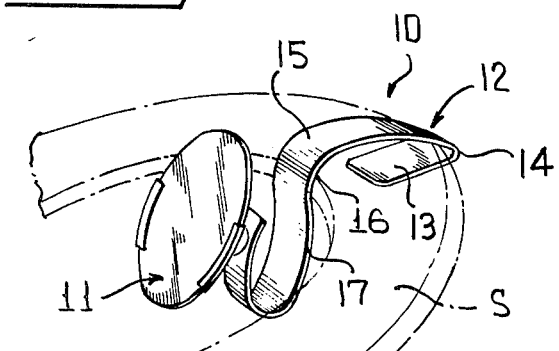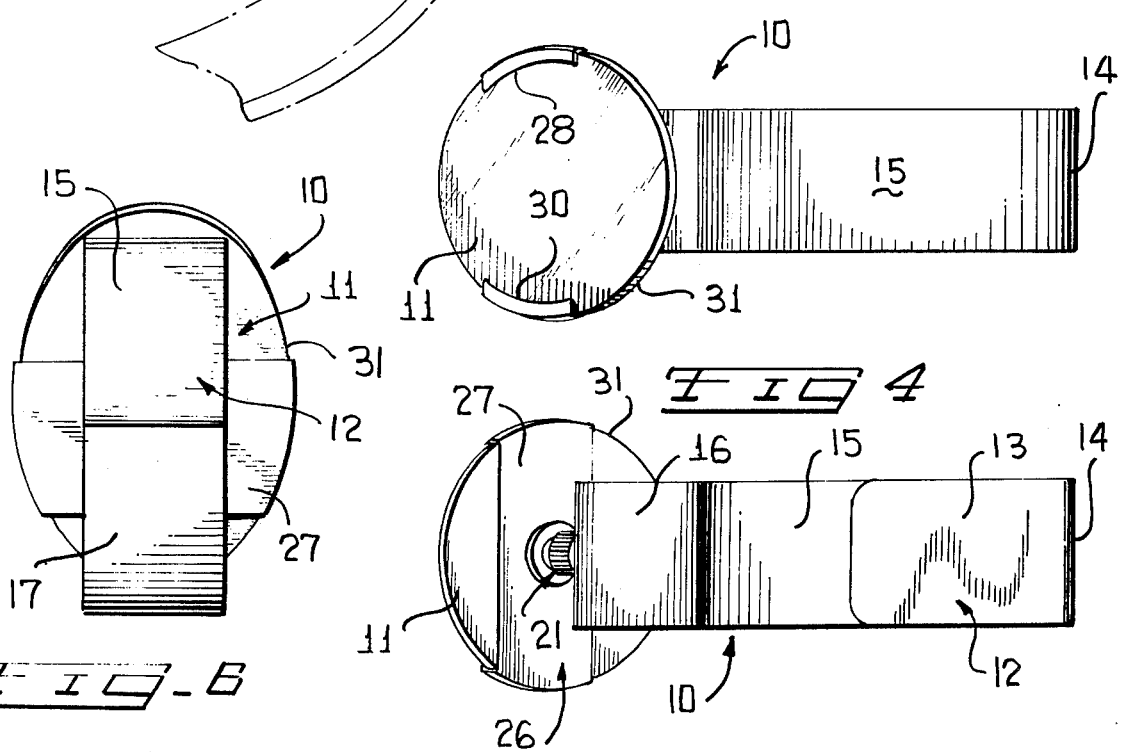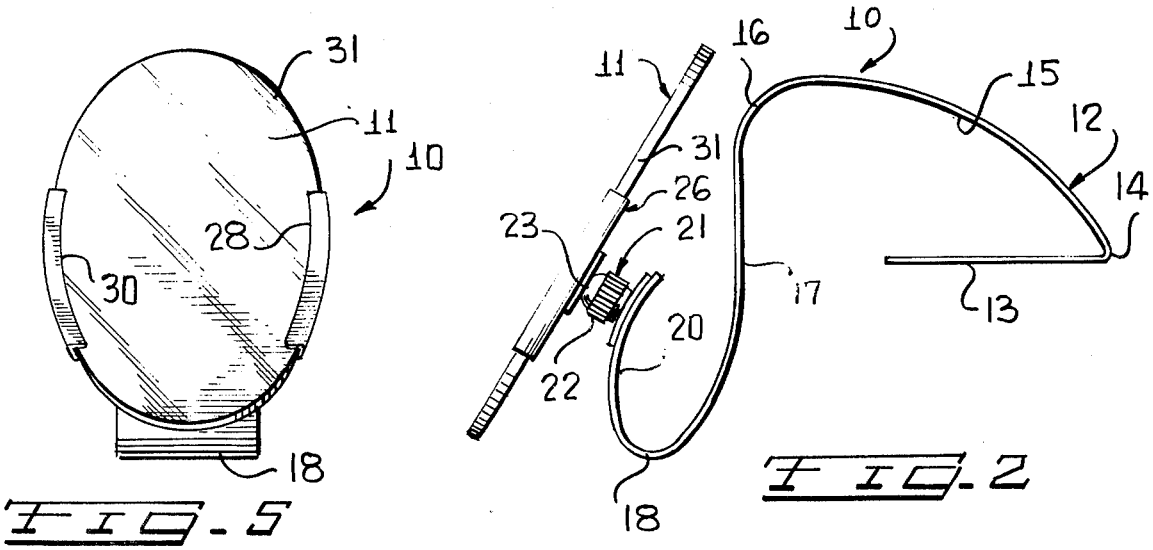

SELF-EXAMINING GENITAL MIRROR

It has become not only common-place but mandatory for both males and females to assure hygienic care and other essentials by the visual inspection of the vaginal and/or genital areas. However, heretofore, means for accommodating such necessary purposes have been totally unavailable commercially or otherwise. As an example, the now most mandatory requirement of female self-administered Pap-tests requires the guidance which would be provided by the device of the present invention. Though the latter is an exemplatory illustration of the purpose of this invention, it is certainly not all inclusive, and the uses, therefore, are not applicable to females alone, but also to males.

In keeping with the foregoing, a primary objective of this invention is to provide a device to effect the foregoing objectives, particularly by the provision of a mirror for visually inspecting the vaginal and/or genital areas of a person preferably while in a seated position, and means for attaching the mirror to a toilet and/or commode seat.

Another objective of this invention is to provide a device wherein the attaching means is generally of an S-shaped configuration.

A further objective of this invention is to provide a device particularly adapted for hygienic purposes which also includes the aforementioned mirror means for visually inspecting the vaginal, and/or genital area of a person, and said mirror means is preferably double-sided, such that normal vision would be achieved by one side and enlarger vision would be achieved by the other side.

With these and the other objectives in view that will hereinafter appear, the nature and scope of the present invention will be more readily apparent by the accompanying drawings;

IN THE DRAWINGS

FIG. 1 is a fragmentary perspective view of a toilet seat, and illustrates the device of this invention which includes mirror means for inspecting the vaginal and/or genital areas, and additionally includes means for attaching the latter to said toilet and/or commode seat.

FIG. 2 is a side elevational view of the device of this invention, and illustrates the attaching means in the form of generally inverted S-shaped bendable piece of metallic or plastic material.

FIG. 3 is a top plan view of the device of this invention, and particularly illustrates the manner in which the mirror is attached to the toilet seat.

FIG. 4 is a bottom plan view of the device of this invention and illustrates not only the manner in which the mirror is attached, but also the provision of securing the mirror to the attached means.

FIG. 5 is an elevational view looking from left-to-right of FIG. 2, and more specifically illustrates the manner in which the mirror is joined to the attaching means.

FIG. 6 is a side elevational view of the device of this invention looking from right-to-left as viewed in FIG. 2 and particularly illustrates the manner in which an end portion of the attaching means is bent toward the mirror and attached to the toilet and/or commode seat.

Reference is made to FIG. 1 of the drawing which discloses the novel device of this invention generally designated by the reference numeral 10. The device 10 is particularly adapted for hygienic purposes and comprises mirror means 11 for visually inspecting the vaginal and/or genital area of a person particularly while in a seated position. The device 10 includes means 12 for attaching the mirror or mirror means 11 to a toilet or commode seats or the like.

The attaching means 12 is of a generally S-shaped configuration (FIG. 2) when viewed in side elevation. The attaching means 12 includes a free terminal end portion 13 (FIG. 2) joined by an abrupt radius 14 to a concavely downwardly opening shaped portion 15 which is preferably contoured to the general configuration of the upper surface of the toilet seats (FIG. 1). The portion 15 merges in a gradual bend 16 to a depending portion 17 which in turn merges to another less gradual bend 18 to an end portion 20 opposite to the terminal end portion 13.

The entire attaching means 12 which includes the portions 13 through 18 and 20 is preferably constructed from bendable material as, for example, malleable metallic material but the same may also be constructed from plastic material and preferably in the case of the former the under surface of the portions 16, 15 and 14 as viewed in FIG. 2 and the upper surface of the portion 13 as viewed in FIG. 2 is coated or otherwise provided with non-marring material such as cloth, foam, felt or the like to assure that the upper and lower surfaces of the seats of FIG. 1 are not marred and/or otherwise obliterated during the use of device 10.

Welded, braised or otherwise secured to the end portion 20 of the attaching means 12 is a threaded stud 21 upon which is threadably secured a nut 22 carrying a universal joint or connection 23. The universal joint 23 assures that the mirror means 11 can be adjusted as might be required by the person employing and/or using the hygienic device 10. The ball end (unnumbered) of the universal joint 23 is welded, soldered or otherwise attached to means 26 for holding the mirror means or mirror 11. The mirror holding means 26 may be a piece of metallic material, or may be plastic material or the like, which in transverse cross-section is of a generally shallow U-shaped configuration including a bight portion 27 having arms 28 and 30 which are bent toward each other in the manner readily apparent from FIGS. 1, 3 and 5 of the drawing. The arms 28 and 30 are in opposed concave configuration to snugly receive the mirror 11 which is contoured about its periphery 31 to downwardly slidingly though releaseably engaged the inner most surface (unnumbered) of the arms 28, 30.

In other words, though the universal joint 23 provides total adjustability for visual inspection, the entire attaching portion 12 may also be bent as desired for any angle desired. Moreover, the bendable nature of the material, metallic, plastic or the like is also desirable in order that the portions 13 through 15 may be likewise bent to accommodate the particular contour of different seats.

In view of the foregoing, the novel device 10 of this invention permits total hygienic observation and evaluation of those areas which over the last several years have been described as requiring evaluation for self-perpetuation.

In view of this construction, the attaching means 12 and the mirror 11 can be compactly carried in unassembled relationship and yet can be advantageously united by simply inserting the mirror 11 into the arms 28, 30 in the manner readily apparent from FIGS. 2 and 5.

The device 10 is preferably though not necessarily, attached to the seats in the manner illustrated in FIG. 1 such that a person, male or female, may employ the mirror to visually inspect the vaginal and/or genital areas. The latter desirable function is also augmented by the universal adjustment of the means 23 and the bendable nature of the material from which the attaching means 12 is constructed.

Although only a preferred embodiment of the invention has been specifically illustrated and described herein, minor variations may be made in the device without departing from the spirit of the invention, as defined by the appended claims.

What is claimed is:

1. A device particularly adapted for hygienic purposes comprising mirror means for visibly inspecting the vaginal and/or genital area of a person while in a seated position, bendable shape retaining means for conformingly attaching said mirror means to a toilet seat, said attaching means includes a generally C-shaped end portion for embracing attachment to a toilet seat, and said C-shaped end portion includes a generally flat uniplanar end for engagement beneath a toilet seat and an adjacent concavely curved portion adjusted to correspond generally to the curvature of the upper surface of a toilet seat.

2. A device particularly adapted for hygienic purposes comprising mirror means for visibly inspecting the vaginal and/or genital area of a person while in a seated position, bendable shape retaining means for confirmingly attaching said mirror means to a toilet seat, means are provided for joining said mirror means to said attaching means, and said joining means include opposing channel means converging downwardly for receiving and supporting therebetween a mirror.

3. A device particularly adapted for hygienic purposes comprising mirror means for visibly inspecting the vaginal and/or genital area of a person while in a seated position, bendable shape retaining means for conformingly attaching said mirror means to a toilet seat, said attaching means is a generally elongated flat strip of bendable material which in longitudinal cross-section is of a generally S-shaped configuration having opposite terminal end portions, a first of said terminal end portions being joined to said mirror means, a second of said terminal end portions constituting said attaching means, and said second terminal end portion having a free end directed toward said first terminal end portion.

4. The device as defined in claim 3 wherein said terminal end is flat and uniplanar.

* * * * *